(12) United States Patent
Ardon et al.

(10) Patent No.: US 10,743,844 B2
(45) Date of Patent: Aug. 18, 2020

(54) ULTRASOUND IMAGING APPARATUS

(71) Applicant: KONINKLIJKE PHILIPS N.V., Eindhoven (NL)

(72) Inventors: Roberto Jose Ardon, Sévres (NL); Remi Nicolas Thierry Cuingnet, Eindhoven (NL); Jean-Michel Rouet, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 606 days.

(21) Appl. No.: 15/327,426

(22) PCT Filed: Jul. 14, 2015

(86) PCT No.: PCT/EP2015/066036
§ 371 (c)(1),
(2) Date: Jan. 19, 2017

(87) PCT Pub. No.: WO2016/015994
PCT Pub. Date: Feb. 4, 2016

(65) Prior Publication Data
US 2017/0181730 A1 Jun. 29, 2017

(30) Foreign Application Priority Data
Jul. 29, 2014 (EP) .................................. 14306212

(51) Int. Cl.
*A61B 8/08* (2006.01)
*G01S 7/52* (2006.01)
(Continued)

(52) U.S. Cl.
CPC .......... *A61B 8/5246* (2013.01); *A61B 8/0866* (2013.01); *A61B 8/145* (2013.01);
(Continued)

(58) Field of Classification Search
CPC ......... A61B 8/5246; A61B 8/54; A61B 8/461; A61B 8/5207; A61B 8/4444;
(Continued)

(56) References Cited

U.S. PATENT DOCUMENTS 5,655,535 A  8/1997  Friemel et al.
6,117,081 A  9/2000  Jago et al.
(Continued)

FOREIGN PATENT DOCUMENTS

CN  100998511 A  7/2007
JP  2008194476 A  8/2008
(Continued)

OTHER PUBLICATIONS

G. Malinger et al., "Sonographic examination of the fetal central nervous system: guidelines for performing the basic examination and the fetal neurosonogram." Ultrasound Obstet Gynecol, vol. 29, pp. 109-116, 2007.

(Continued)

*Primary Examiner* — Mark Bockelman

(57) ABSTRACT

An ultrasound imaging apparatus (20) is disclosed, comprising a data interface (30) configured to receive a plurality of different ultrasound data sets (26, 28) resulting from an ultrasound scan of an object (18) in different viewing directions. The ultrasound imaging apparatus further comprises a segmentation unit (32) for segmenting anatomical structures of the object in the different ultrasound data sets and for providing segmentation data of the anatomical structures, and a reference determining unit (34) for determining a spatial reference (48, 50, 52, 54) for the different ultrasound data sets on the basis of the segmentation data. A confidence determining unit (40) is included for determining confidence values (56) for different regions of the received ultrasound data on the basis of the spatial reference.

11 Claims, 8 Drawing Sheets

(51) Int. Cl.
*G01S 15/89* (2006.01)
*A61B 8/00* (2006.01)
*A61B 8/14* (2006.01)

(52) U.S. Cl.
CPC ............ *A61B 8/4444* (2013.01); *A61B 8/461* (2013.01); *A61B 8/483* (2013.01); *A61B 8/5207* (2013.01); *A61B 8/5253* (2013.01); *A61B 8/5269* (2013.01); *A61B 8/54* (2013.01); *G01S 7/52071* (2013.01); *G01S 7/52074* (2013.01); *G01S 15/8925* (2013.01); *G01S 15/8936* (2013.01); *G01S 15/8993* (2013.01); *G01S 15/8995* (2013.01)

(58) Field of Classification Search
CPC ... A61B 8/0866; A61B 8/5269; A61B 8/5253; A61B 8/483; A61B 8/145; G01S 15/8936; G01S 15/8925; G01S 7/52074; G01S 7/52071; G01S 15/8993; G01S 15/8995
See application file for complete search history.

(56) References Cited

U.S. PATENT DOCUMENTS

| | | | |
|---|---|---|---|
| 6,135,956 | A | 10/2000 | Schmiesing et al. |
| 6,374,674 | B1 | 4/2002 | Mine |
| 7,736,313 | B2 | 6/2010 | Luo et al. |
| 8,556,814 | B2 | 10/2013 | Carneiro et al. |
| 8,574,157 | B2 | 11/2013 | Hoctor et al. |
| 9,360,551 | B2 | 6/2016 | Umezawa et al. |
| 2004/0158154 | A1 | 8/2004 | Hanafy et al. |
| 2006/0098864 | A1 | 5/2006 | Ziel |
| 2006/0120608 | A1 | 6/2006 | Luo et al. |
| 2006/0274928 | A1 | 12/2006 | Collins et al. |
| 2007/0223794 | A1* | 9/2007 | Preiss ............... A61B 8/12 382/128 |
| 2009/0093717 | A1 | 4/2009 | Carneiro et al. |
| 2013/0261463 | A1 | 10/2013 | Chiang et al. |
| 2013/0294665 | A1 | 11/2013 | Rao et al. |
| 2014/0187953 | A1 | 7/2014 | Miyachi et al. |
| 2015/0306426 | A1 | 10/2015 | Dehghan Marvast et al. |

FOREIGN PATENT DOCUMENTS

| | | |
|---|---|---|
| JP | 2010514486 A | 5/2010 |
| JP | 2013255697 A | 12/2013 |
| WO | 2008078265 A2 | 7/2008 |

OTHER PUBLICATIONS

M. Kuklisova-Murgasova et al., "Registration of 3D Fetal Brain US and MRI," in MICCAI. 2012, vol. 7511 of LNCS, pp. 667-674, Springer.

R. Cuingnet, O. Somphone, B. Mory, R. Prevost, M. Yaqub, R. Napolitano, A. Papageorghiou, D. Roundhill, J.A. Noble, R. Ardon, Where is my Baby? A Fast Fetal Head Auto-Alignment in 3D-Ultrasound, Proceedings of the the IEEE International Symposium on Biomedical Imaging (ISBI) 2013: from Nano to Macro, Apr. 2013, San Francisco, CA, USA.

J.A. Jensen: A Model for the Propagation and Scattering of Ultrasound in Tissue, J.Acoust.Soc.Am. 89, pp. 182-191, 1991.

Karamalis, Athanasios, Wein, Wolfgang, et Navab, Nassir. Fast ultrasound image simulation using the westervelt equation. In : Medical Image Computing and Computer-Assisted Intervention—MICCAI 2010. Springer Berlin Heidelberg, 2010. p. 243-250.

Correa et al "Examination of the Fetal Brain by Transabdominal Three-Dimensional Ultrasound . . . " Ultrasound Obstet Gynecol. 2006, vol. 27 p. 503-508.

Pooh et al Clinical Application of Three-Dimensional Ultrasound in Fetal Brain Assessment, Croatian Medical Journal, vol. 41, vol. 3 p. 245-251 (2000).

Monteagudo et al Three Dimensional Transvaginal Neurosonography of the Fetal Brain:Navigating in the Volume Scan, Ultrasound Obset. Gynecol. 2000 16, p. 307-313.

* cited by examiner

ULTRASOUND IMAGING APPARATUS

This application is the U.S. National Phase application under 35 U.S.C. § 371 of International Application No. PCT/EP2015/066036, filed on Jul. 14, 2015, which claims the benefit of EP Application Serial No. 14306212.3 filed Jul. 29, 2014. These applications are hereby incorporated by reference herein.

FIELD OF THE INVENTION

The present invention relates to an ultrasound imaging apparatus. An exemplary technical application of the present invention is the generation of two-dimensional images of a foetal skull based on one or more acquired three-dimensional ultrasound scans. The present invention further relates to an ultrasound imaging system for determining ultrasound image data from an object. The present invention further relates to a method for evaluating ultrasound image data from an anatomical site of an object and finally to a computer program comprising program code means for causing a computer to carry out a method for evaluating ultrasound image data from an anatomical site of an object.

BACKGROUND OF THE INVENTION

Ultrasound imaging systems are generally known for examination of anatomical features in human patients. In particular, ultrasound imaging systems are used for prenatal screening examination of the foetal central nervous system. A corresponding ultrasound system is e.g. known from US 2009/0093717 A1.

Due to the physics of ultrasound propagation in tissue, the orientation of the ultrasound probe with respect to the anatomical features and in particular with respect to a foetal skull has a significant influence on the quality of the ultrasound images and in this particular case of the neurosonogram. To overcome this drawback of the ultrasound propagation in tissue, the probe of the ultrasound system is usually disposed at a specific position in order to obtain the most confident view for diagnostic.

A further technique to improve the quality of the ultrasound images is to acquire a series of partially overlapping image frames from independent spatial directions using a transducer array for steering and/or translation of the different image frames.

However, the known ultrasound imaging systems cannot reflect the anatomical structures of all regions within the field of view and may provide artefacts in certain regions of the field of view so that the clinical diagnostic can be negatively affected.

SUMMARY OF THE INVENTION

It is an object of the present invention to provide an improved ultrasound imaging apparatus, which allows a more comfortable and more reliable analysis of ultrasound data of an anatomical object, e.g. of a skull of a foetus. It is furthermore an object of the present invention to provide a corresponding method and a computer program for implementing such method.

In a first aspect of the present invention, an ultrasound imaging apparatus is presented comprising:

a data interface configured to receive a plurality of different ultrasound data sets resulting from an ultrasound scan of an object in different viewing directions, a segmentation unit for segmenting anatomical structures of the object in the different ultrasound data sets and for providing segmentation data of the anatomical structures, a reference determining unit for determining a spatial reference for the different ultrasound data sets on the basis of the segmentation data, and an image generation unit for combining the different ultrasound data sets to a compound ultrasound image on the basis of the different spatial references.

In a further aspect of the present invention an ultrasound imaging apparatus is presented comprising:

a data interface configured to receive ultrasound data resulting from an ultrasound scan of an object, p a segmentation unit for segmenting anatomical structures of the object in the ultrasound data and for providing segmentation data of the anatomical structures, a reference determining unit for determining a spatial reference for the ultrasound data on the basis of the segmentation data, and a confidence determining unit for determining confidence values for different regions of the received ultrasound data on the basis of the spatial reference.

In a further aspect of the present, a method for evaluating ultrasound image data from an anatomical site of an object is presented comprising the steps of:

receiving at least one ultrasound data set of the object from different viewing directions, segmenting anatomical structures in the ultrasound data set and providing segmentation data of the anatomical structures, determining a spatial reference for the ultrasound data set on the basis of the segmentation data, determining (88, 76) confidence values (56) of the received ultrasound data on the basis of the spatial reference; and combining the different ultrasound data sets to a compound ultrasound image on the basis of the different spatial references and the confidence values, wherein the ultrasound data of the different regions in the different ultrasound data sets are weighted on the basis of the different confidence values to form the compound image.

In a still further aspect of the present invention, a computer program is presented comprising program code means for causing a computer to carry out the steps of the above-mentioned method when said computer program is carried out on the computer.

It shall be understood that the claimed method has similar and/or identical preferred embodiments as the claimed ultrasound imaging apparatus and as defined above and as defined in the dependent claims.

The present invention is based on the idea to generate a compound ultrasound image on the basis of ultrasound scans acquired in different viewing directions or different fields of view so that regions of the scanned object which may be shadowed or masked in the ultrasound image due to the physics of ultrasound propagation in the tissue can be reduced. The orientation of the different ultrasound data or the different viewing directions are identified by segmentation of anatomical structures of the object and certain reference structures are identified within the data so that the image generation unit can reorient the ultrasound data in order to form the compound ultrasound image on the basis of the different ultrasound data acquired in the different viewing directions. Consequently, a high quality compound ultrasound image can be provided in real time with low technical effort, so that the acquiring of the ultrasound image is more comfortable and the quality is increased. A further idea of the present invention is to determine confidence values for different regions of the ultrasound data in order to identify those regions in the ultrasound data, which may have a low quality due to the ultrasound propagation in the tissue so that the areas of low quality or low confidence can be identified and an indication can be provided to the user. Hence, a wrong clinical diagnosis due to artefacts can be reduced and the reliability of the ultrasound imaging is increased. The ultrasound data of the different regions in the different ultrasound data sets can be weighted on the basis of the different confidence values, such that the formed compound image has a further improved quality.

Confidence values for different regions of the ultrasound data in the meaning of the present invention are values corresponding to an expected quality and/or reliability of the measured ultrasound data which may influence a diagnosis based on the ultrasound images.

In a preferred embodiment, the spatial references comprise a reference frame including at least one reference position and one reference direction of the object. This is a possibility to identify a relative position and an orientation of the anatomical object in the field of view in order to combine the different ultrasound data sets to the compound ultrasound image with high reliability.

In a preferred embodiment, the reference determining unit is adapted to determine a spatial transformation between two ultrasound data sets on the basis of the respective spatial references. This is a possibility to calculate or transform each voxel of the different ultrasound data sets to one voxel of the compound ultrasound image so that the compound ultrasound image can be compounded with low processing effort and low time consumption so that an almost real time image can be produced.

In a preferred embodiment, the spatial transformation comprises a spatial translation and a rotation of the corresponding ultrasound data sets. This is a further possibility to reduce the processing effort since the transformation can be calculated from the spatial reference with reduced calculation steps.

In a preferred embodiment, the data interface is adapted to receive the ultrasound data sets substantially simultaneously to the ultrasound scan of the object as consecutive data sets or a substantially continuous data stream, and wherein the image generation unit is adapted to generate the compound image substantially simultaneously to the received data sets. This is a possibility to provide the compound ultrasound image in real time, since the scan of the object, the transmission of the data sets, the processing of the data and the generation of the compound ultrasound image are substantially simultaneously so that a display of the compound ultrasound image can be provided in real time almost synchronously to the respective scan. It shall be understood that substantially simultaneously according to the invention means that a delay between the scan, the data transmission and the processing of the data in order to form the compound ultrasound image may be present due to the corresponding data processing steps and that the delay is in the range of less than a sec.

In a preferred embodiment, the image generation unit is adapted to combine the received ultrasound data sets with a previously generated compound ultrasound image in order to adjust the compound ultrasound image continuously. In other words, the compound ultrasound image is generated at the beginning of a scan and continuously adjusted or improved on the basis of the additional ultrasound data sets received consecutively or continuously during the ongoing ultrasound scan. This is a possibility to improve the compound ultrasound image continuously until a level of quality is achieved, which is necessary for a clinical diagnosis.

In a preferred embodiment, the image generation unit is adapted to stop the compound ultrasound image generation automatically or upon request of a user, if a desired resolution of the compound image or a desired quality of the compound image is achieved.

In a further preferred embodiment, the ultrasound imaging apparatus comprises a confidence determining unit for determining confidence values for different regions of the received ultrasound data sets on the basis of the spatial references. The confidence values represent a level of expected reliability or quality of the acquired and received ultrasound data for different regions. The confidence values are preferably determined on the basis of the physics of ultrasound propagation in tissue, the orientation of the ultrasound probe with respect to the anatomical structures of the object so that a quality of the received ultrasound data in the different regions can be determined. This is a possibility to identify regions in the received ultrasound data of low quality or potentially low quality so that measures to overcome this reduced quality can be taken by the user, e.g. that the user does not consider the regions of low confidence values for clinical diagnosis or performs additional scans or analysis in those regions in order to improve the confidence level.

In a preferred embodiment, the reference determining unit is adapted to determine a spatial orientation of the anatomical object in a field of view of the ultrasound scan on the basis of the spatial reference, and wherein the confidence determining unit is adapted to determine the confidence values on the basis of the spatial orientation of the anatomical object in the field of view. This is a possibility to identify regions of low confidence values easily since e.g. shadowed area can be identified.

In a preferred embodiment, the confidence values are determined on the basis of predetermined reference values of the different regions of the object. This is a possibility to determine the confidence values with low technical effort, since the values are predefined in the values can be determined e.g. on the basis of experience values for regions of high and/or low confidence levels.

In a preferred embodiment, the confidence values are determined on the basis of a propagation model of the anatomical object for the ultrasound waves. This is a possibility to consider the physics of the ultrasound propagation in the tissue of the object so that the confidence values can be determined with high precision.

In a preferred embodiment, one confidence value is assigned to each voxel of the ultrasound data and the confidence values are stored in a confidence map. This is a possibility to link the voxels of the ultrasound data sets with an individual confidence value so that a calculation of the voxel data and the confidence data can be easily processed.

In a preferred embodiment, the compound image is generated on the basis of the confidence values, wherein the ultrasound data of the different regions in the different ultrasound data sets are weighted on the basis of the different confidence values to form the compound image. This is a possibility to improve the quality of the compound image, since the ultrasound data of low confidence regions are less considered and the ultrasound data of the regions having a high confidence level are considered more.

In a preferred embodiment, the image generation unit is adapted to provide a graphical representation of the confidence values within the compound image. In a further preferred embodiment, the confidence values are displayed as an image structure superposed to the ultrasound data. This is a possibility to improve the visibility of the regions having high or low confidence so that a simple feedback to the user can be provided.

As mentioned above, the present invention provides a possibility to improve the reliability of ultrasound images, since the ultrasound data is captured in different viewing directions and composed to a compound image on the basis of structural references, which are determined in the ultrasound image data by means of a segmentation of the anatomical structures. Due to the different viewing directions of the ultrasound probe capturing the ultrasound data sets, the amount of regions of the object with low ultrasound data quality can be reduced, since e.g. shadowed regions can be minimized. Since the compound ultrasound image is processed on the basis of the references in the ultrasound data which are determined on the basis of the anatomical structures, the different data sets can be compounded or assembled to the compound ultrasound image with low technical effort so that a high quality compound ultrasound image can be achieved. Further, since the confidence values for different regions in the ultrasound data are determined corresponding to a quality or a reliability of the ultrasound image data, the reliability of the ultrasound analysis can be improved, since the confidence value can be considered during the composition of the composed ultrasound image or the confidence values can be displayed in the displayed ultrasound image so that the operator can easily identify the regions of high and low quality.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
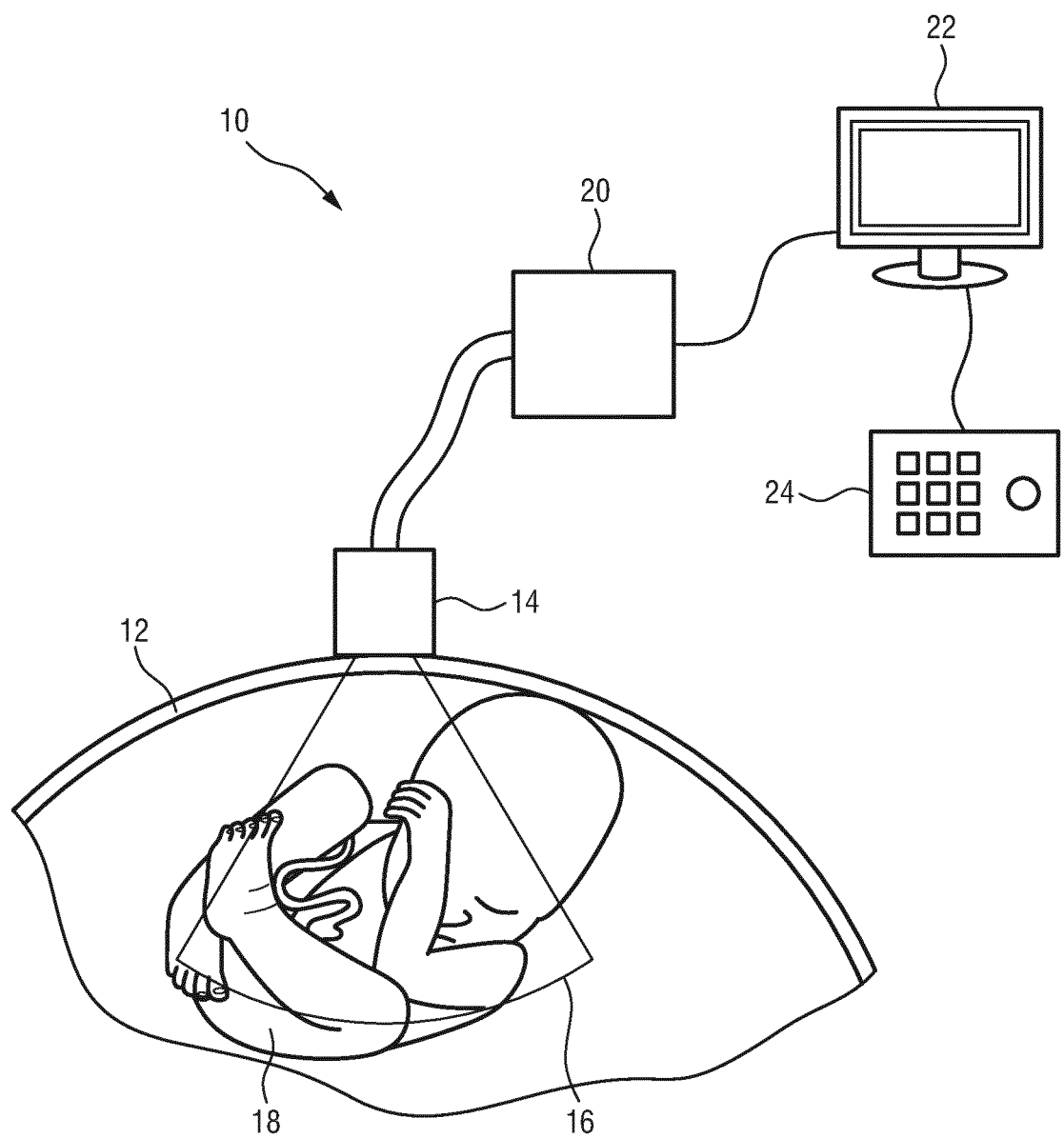
FIG. 1 shows a schematic representation of an ultrasound imaging system in use to scan a volume of a patient's body including a foetus.

FIG. 1 shows a schematic illustration of an ultrasound imaging system according to an embodiment generally denoted by 10. The ultrasound imaging system 10 is applied to inspect a volume of an anatomical site, in particular an anatomical site of a patient 12. The ultrasound imaging system 10 comprises an ultrasound probe 14 having at least one transducer array having a multitude of transducer elements for transmitting and/or receiving ultrasound waves. The transducer elements are preferably arranged in a two-dimensional array, in particular for providing a multi-planar or three-dimensional image. The probe 14 is adapted to transmit ultrasound waves in a particular direction and to receive ultrasound waves from a particular direction which forms a field of view 16 of the ultrasound probe 14.

In the embodiment shown in FIG. 1, the patient 12 is a pregnant person, wherein an anatomical object to be inspected is a foetus 18, which is disposed in the field of view 16.

Due to the physics of the ultrasound propagation in tissue, certain regions in the field of view 16 may not reflect the anatomical structures of the object 18 since some areas may be shadowed or masked by other anatomical structures within the ultrasound propagation path. This is a general problem of ultrasound analysis methods and is in particular a problem of prenatal neurosonograms which is as an example shown in FIG. 1, since any ultrasound data acquired by the probe 14 also with different probe positions and different viewing directions of the probe 14 include different regions which are not accurately reflected and which have a low confidence level and/or a low quality. As described in the following, the ultrasound system 10 produces a compound ultrasound image by combining different ultrasound data sets resulting from an ultrasound scan of the object 18 in different viewing directions so that the amount of image quality defects can be reduced.

The ultrasound imaging system 10 further comprises an ultrasound imaging apparatus 20 such as a control unit, which controls the provision of an ultrasound image via the ultrasound system 10. As will be explained further below, the ultrasound imaging apparatus 20 receives ultrasound image sets from the transducer array of the ultrasound probe 14 and provides a three-dimensional ultrasound image derived from the different ultrasound data sets of the object 18.

The ultrasound imaging system 10 may further comprise a display 22 for displaying the ultrasound image received from the ultrasound imaging apparatus 20. Still further, an input device 24 may be provided that may comprise keys or a keyboard and further inputting devices and may be connected to the display 22 or directly to the ultrasound imaging apparatus 20.

Figure 2:
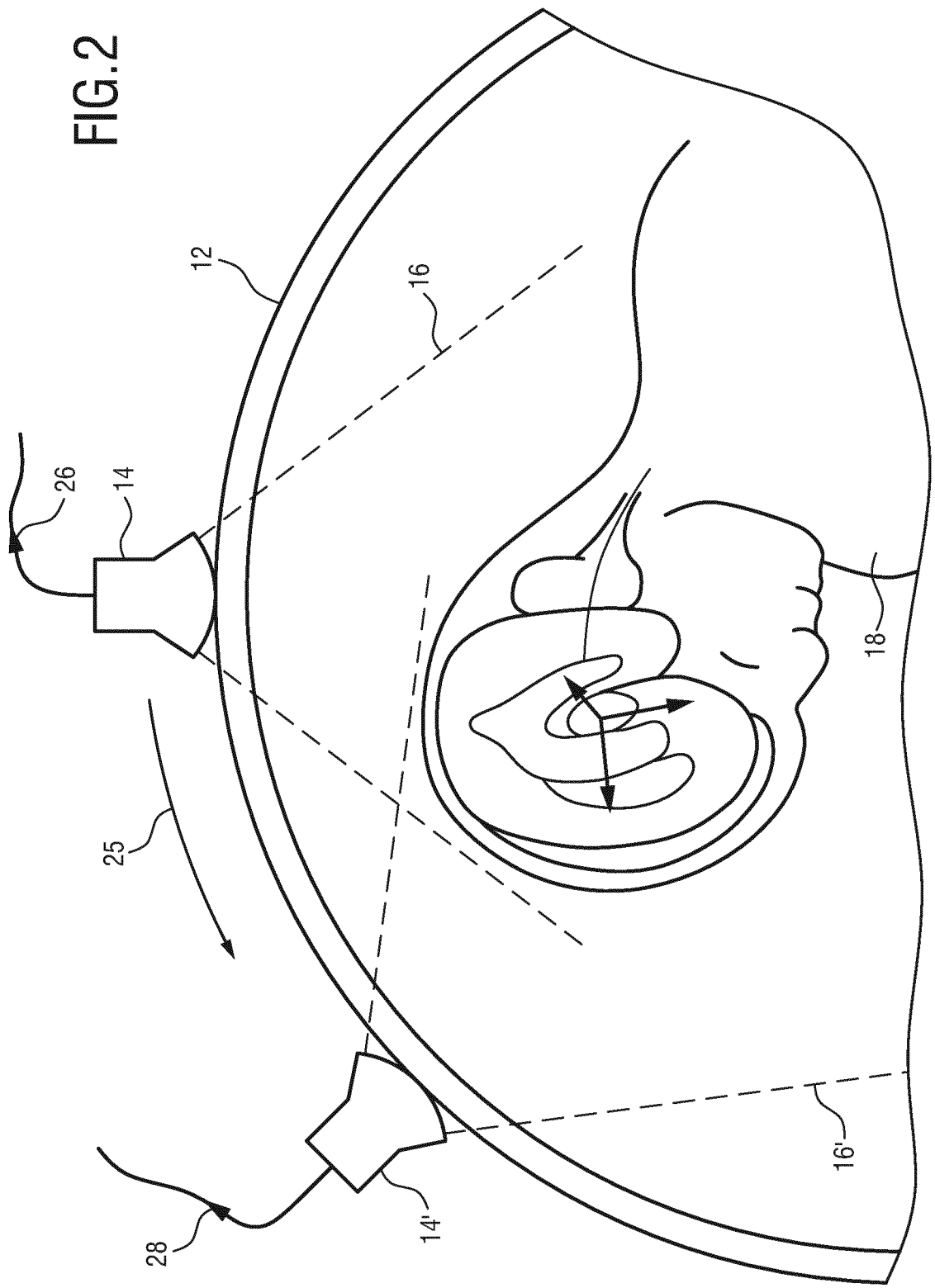
FIG. 2 shows a schematic illustration of different ultrasound scans in different viewing directions.

In FIG. 2 a schematic perspective diagram is shown for explaining the ultrasound scan of the object 18 from different viewing directions. The probe 14 is moved around the patient's body 12 as indicated by an arrow 25 in order to acquire different ultrasound data sets 26, 28 from the different viewing directions so that the object 18 is differently oriented within the field of view 16, 16' and the regions shadowed or obscured due to the propagation direction of the ultrasound waves can be reduced.

In order to provide a high quality ultrasound image, the ultrasound imaging apparatus 20 combines the different ultrasound data sets 26, 28 of the different viewing directions to a compound ultrasound image on the basis of different spatial references identified in the field of view 16, 16' on the basis of segmented anatomical structures of the object 18 as described in detail in the following.

Figure 3A:
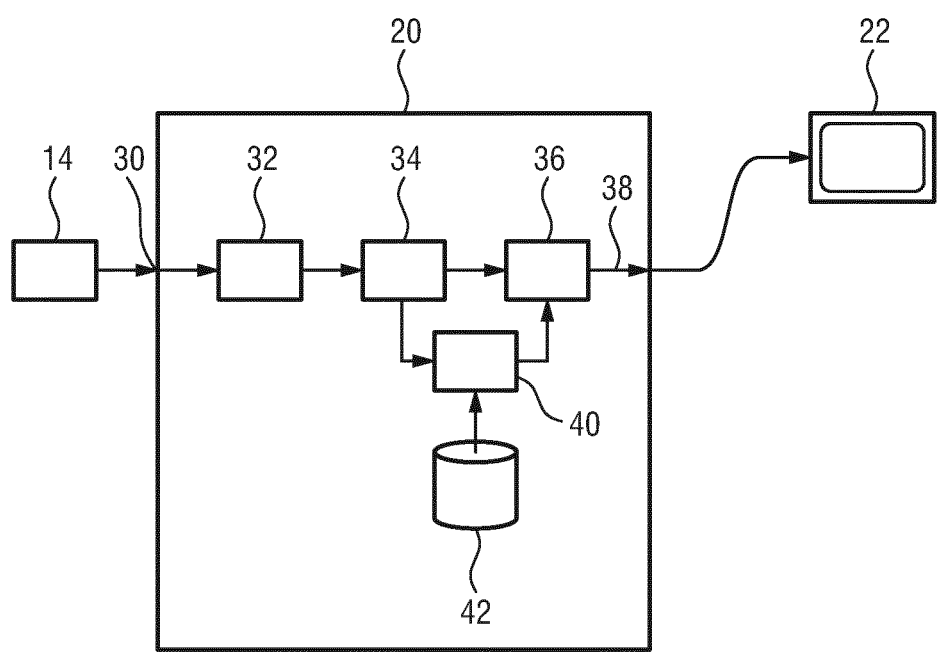
FIG. 3a, b show schematic block diagrams of embodiments of an ultrasound imaging apparatus.

FIG. 3a shows a schematic block diagram of the ultrasound imaging apparatus 20. The ultrasound imaging apparatus 20 comprises a data interface 30 for connecting the ultrasound imaging apparatus 20 to the ultrasound probe 14 and for receiving the ultrasound data sets 26, 28 from the probe 14. The ultrasound imaging apparatus 20 further comprises a segmentation unit 32, which receives the ultrasound data sets 26, 28. The segmentation unit 32 is provided for segmenting and identifying anatomical structures of the object 18 in the ultrasound data sets on the basis of pattern detection. The segmentation unit 32 provides corresponding segmentation data of the anatomical structures to a reference determining unit 34. The reference determining unit 34 determines spatial references in the segmentation data in order to determine the position and orientation of the object 18 within the field of view 16, 16'. The spatial references are preferably anatomical frames comprising a spatial position of the object 18 in the field of view 16, 16' and a direction as an orientation of the object 18 within the field of view 16, 16'. The so determined spatial references are provided together with the corresponding ultrasound data sets to an image generation unit 36. The reference determining unit 34 determines in a preferred embodiment a spatial mathematical transformation between the two different ultrasound data sets 26, 28 which may comprise a spatial translation and a rotation of the ultrasound data sets in order to align the respective ultrasound data of the different sets to each other.

The image generation unit 36 combines the different ultrasound data sets 26, 28 to a compound ultrasound image 38 on the basis of the different spatial references and provides the compound ultrasound image 38 e.g. to the display 22. The image generation unit 36 aligns the different data sets 26, 28 on the basis of the spatial references so that the ultrasound data of the different data sets 26, 28 receives from identical volumes of the object 18 are superposed in the compound ultrasound image 38. Hence, the quality of the compound ultrasound image 38 is improved since the ultrasound data of the different viewing directions are combined. In one embodiment, the image generation unit 36 receives the spatial transformation between two consecutive ultrasound data sets in order to combine the ultrasound image data sets accurately. The spatial transformation can be directly deduced from the spatial references, which includes a reference frame having a reference position and one or preferably three reference directions of the object 18.

The compound ultrasound image 38 is preferably produced in real time corresponding to the acquisition of the ultrasound data sets 26, 28 so that the compound ultrasound image 38 is displayed on the display 22 almost simultaneously to the ultrasound scan. In order to achieve the real time image, the ultrasound data sets 26, 28 are provided to the data interface 30 as consecutive data sets or as a substantially continuous data stream so that a continuous processing of the ultrasound data sets 26, 28 can be performed by means of the ultrasound imaging apparatus 20.

Preferably, the compound ultrasound image 38 is continuously adjusted on the basis of each additionally received ultrasound data set 26, 28 in order to continuously improve the quality of the compound ultrasound image 38. The currently available compound ultrasound image is displayed on the display 22 so that the operator can decide whether additional scans are necessary and from which viewing directions the scans may be acquired and whether the ultrasound scan can be finalized. In an alternative embodiment, the compound ultrasound image 38 is displayed on demand of the operator. The viewing direction of the displayed compound ultrasound image 38 corresponds to a viewing direction of an initial ultrasound data set 26, 28 or may be adjusted to the current viewing direction of the probe 14.

In a preferred embodiment, the ultrasound imaging apparatus 20 further comprises a confidence determining unit 40, which determines confidence values for different regions in the ultrasound data sets 26, 28 corresponding to an expected quality or a reliability value of the ultrasound measurements of the respective regions. The confidence determining unit receives the spatial reference from the reference determining unit 34 and the segmentation data and determines the relative position of the probe 14 with respect to the anatomical features of the object 18 on the basis of the segmentation data. Since the quality and/or reliability of the ultrasound data is dependent on the anatomical structures and the propagation direction of the ultrasound waves, the confidence determining unit 40 can determine confidence values corresponding to the expected quality and/or reliability of the ultrasound data received from the different regions of the object 18.

The confidence determining unit 40 is connected to an internal or external database or a memory 42 and receives in one embodiment a statistical map of confidence regions comprising typical regions of high or low confidence with respect to the propagation direction of the ultrasound waves and the anatomical structures and determines on the basis of the statistical map of values the confidence values for the different regions in the ultrasound data sets 26, 28. In an alternative embodiment, the confidence determining unit 40 receives an acoustical wave propagation model from the memory 42 and determines the confidence values for the different regions on the basis of the propagation model received from the memory 42.

The confidence values are provided to the image generation unit 36 so that the different confidence values can be displayed in the compound ultrasound image 38. In an alternative embodiment, a confidence map is provided by the confidence determining unit 40 as a probability map having a confidence value preferably between 0 and 1 assigned to each voxel of the ultrasound image sets 26, 28. The compound ultrasound image 38 is generated by the image generation unit 36 as a weighted average of the different data sets 26, 28. Since each voxel is differently weighted on the basis of the confidence probability map, a low confidence region will weekly contribute to the final compound ultrasound image 38 and a high confidence region will strongly contribute to the compound ultrasound image 38.

Therefore, the compound ultrasound image 38 can be provided with a high quality and a high reliability due to the different viewing directions and the confidence values determined for the different regions in the ultrasound data sets 26, 28.

Figure 3B:
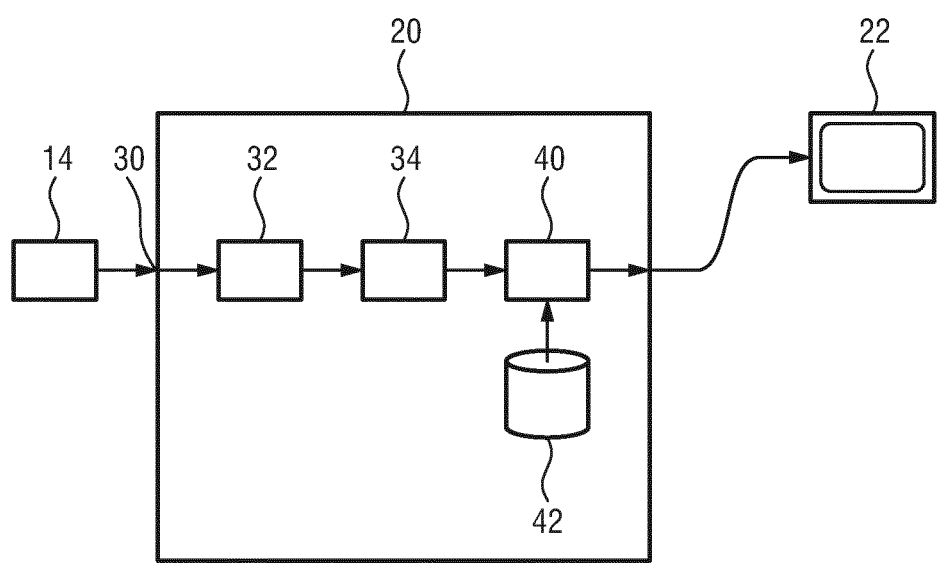

FIG. 3b shows a further embodiment of the ultrasound imaging apparatus 20. Identical elements are denoted by identical reference numerals, wherein here merely the differences are explained in detail. The probe 14 provides an ultrasound data set 26 from one or more viewing directions to the interface 30. The segmentation unit 32 segments anatomical structures of the object 18 and provide segmentation data of the anatomical structures to the reference determining unit 34, which determines a spatial reference in the ultrasound data set 26 on the basis of the segmentation data. The confidence determining unit 40 determines confidence values for different regions in the ultrasound data set 26 on the basis of the determined spatial reference by determining the probe position with respect to the anatomical features of the object 18 as explained above. The confidence values are superposed to the ultrasound data set 26, e.g. as a color overlap or a region contour and provided as image data to the display 22. Hence, the confidence values can be displayed directly in the ultrasound image in order to provide the respective information regarding the probability and/or the quality of the ultrasound data to the user.

The embodiment shown in FIG. 3b is a simple embodiment to indicate that a region of low confidence or low reliability is present in the ultrasound image without acquiring different ultrasound data sets from different viewing directions so that a higher reliability of the ultrasound diagnosis can be achieved with low technical effort.

It shall be understood that the ultrasound imaging apparatus 20 may be a computer and the different components 32, 34, 36, 40 of the ultrasound imaging apparatus 20 may be certain computer program procedures which are executed when a corresponding computer program is executed on the computer.

Figure 4A:
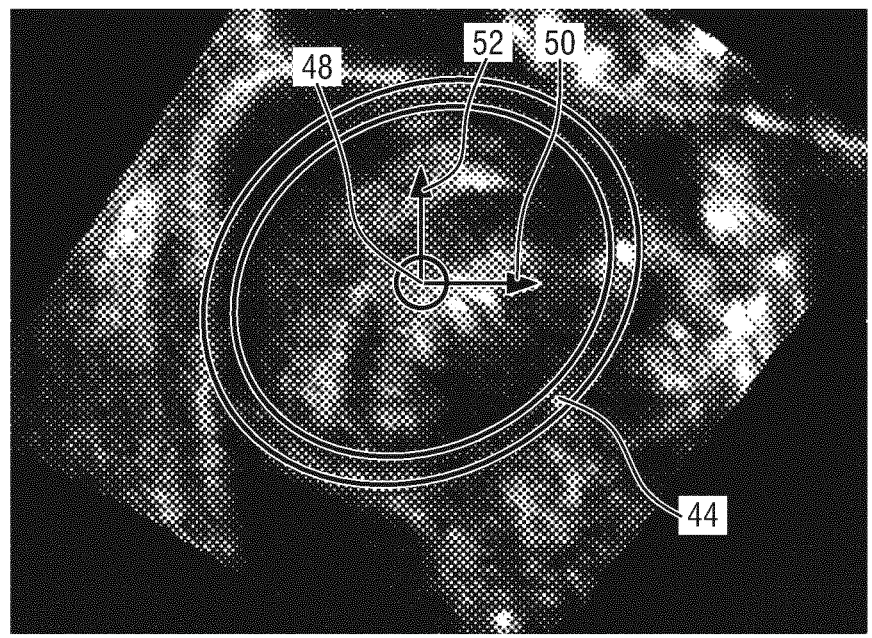
FIG. 4a, b show ultrasound images of a skull of a foetus in different viewing directions including determined reference frames.

FIG. 4a, b show ultrasound images in different viewing directions of the probe 14, wherein the anatomical features of the object 18 are identified by the segmentation unit 32 and the spatial references are determined in each of the ultrasound data sets.

The ultrasound images shown in FIG. 4a, b are captured in different viewing directions as shown in FIG. 2 and comprise a skull of the foetus 18 in the field of view 16. In these ultrasound images the anatomical features of the foetus 18 are identified by the segmentation unit 32 as the skull 44 and the eyes 46. On the basis of the segmentation data a frame of reference is determined including a barycenter 48 of the skull. Further, two vectors 50, 52 are determined which span the mid-sagittal plane, wherein the vector 50 is directed towards the eyes and belongs to the plane generated by the eyes and the barycenter 48 and the vector 52 is directed towards a top of the skull 44. Further, a vector 54 is determined perpendicular to the mid-sagittal plane and oriented so that the frame of reference is positively oriented.

As the probe 14 is moved as indicated in FIG. 2 by the arrow 25, this frame of reference 48-54 is determined so that the orientation of each ultrasound data set 26, 28 can be determined in order to combine the different ultrasound data sets 26, 28 to the compound ultrasound image 38.

Figure 4B:
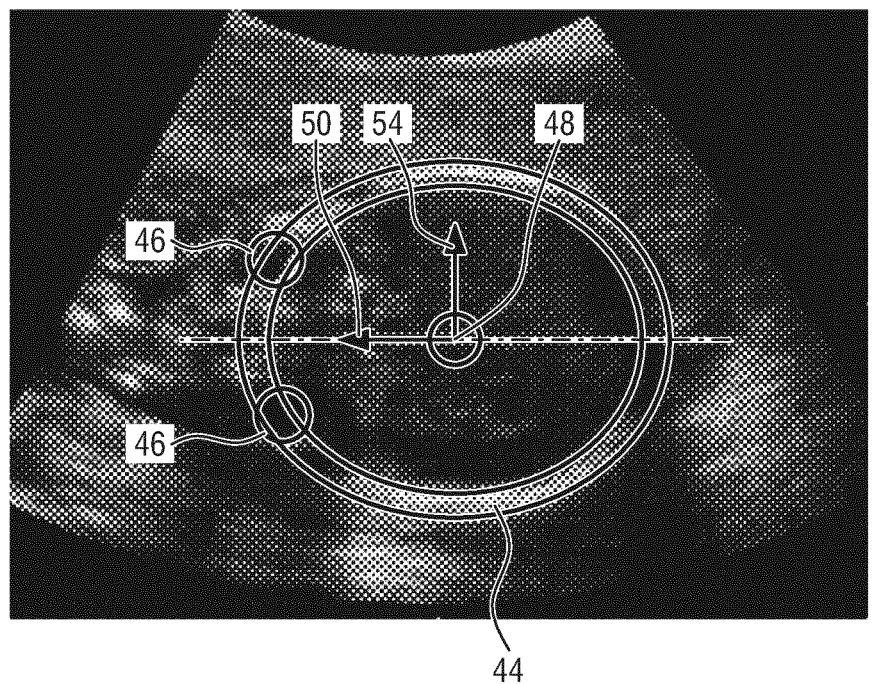
Figure 5A:
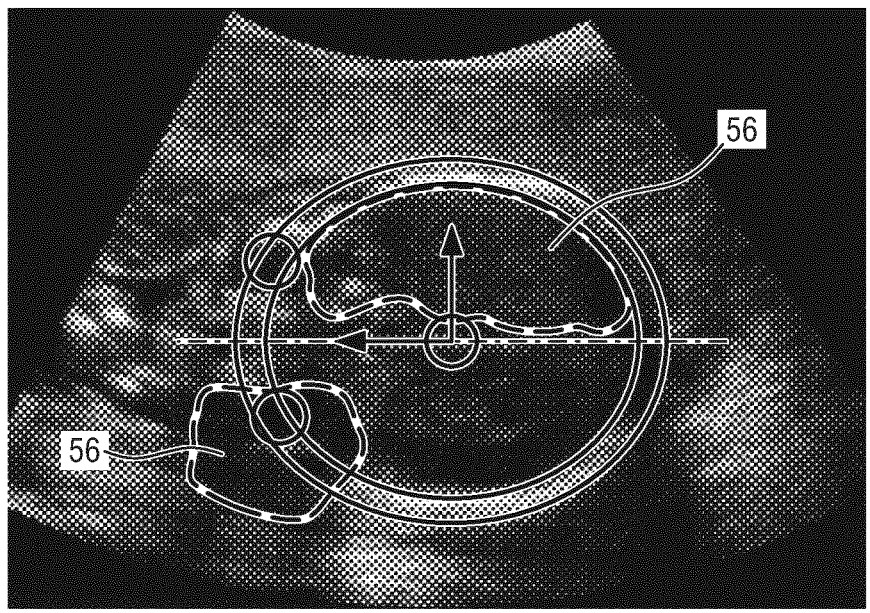
FIG. 5a, b show different ultrasound images including indications of regions of low confidence.

In FIG. 5a, b embodiments of the indication of the confidence values are schematically shown for the ultrasound image shown in FIG. 4b and generally denoted by 56.

In this example, merely the regions in the ultrasound image having a confidence value below a certain confidence level are indicated so that an operator knows that these portions of the image have a reduced quality or a reduced reliability.

In FIG. 5a, the regions of low confidence level are indicated as an overlay contour superposed to the ultrasound image.

Figure 5B:
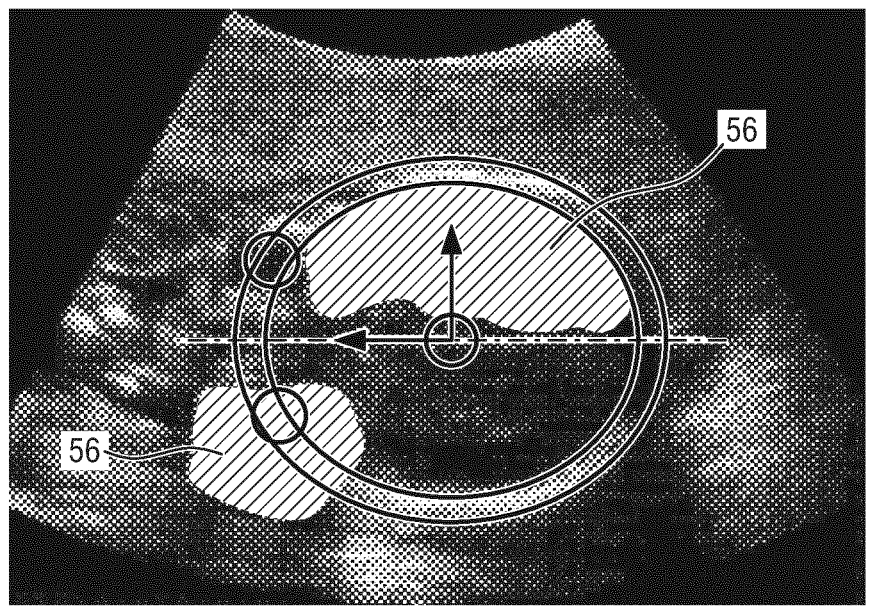

In FIG. 5b, the low confidence region 56 is displayed as a color overlay superposed to the ultrasound image.

Whenever the user initiates a measurement in a region of low confidence 56, an alarm may be raised to the user like a pop-up warning message, a color coded measurement feedback, a sound or the like. Alternatively, when the image is used for a clinical diagnosis, e.g. saved in the system and contains large low confidence region 56, a warning message or an overlay is displayed.

If a large low confidence region 56 is detected, the operator can restart a measurement with a different viewing direction of the probe 14 in order to achieve an ultrasound image having a better quality.

Figure 6A:
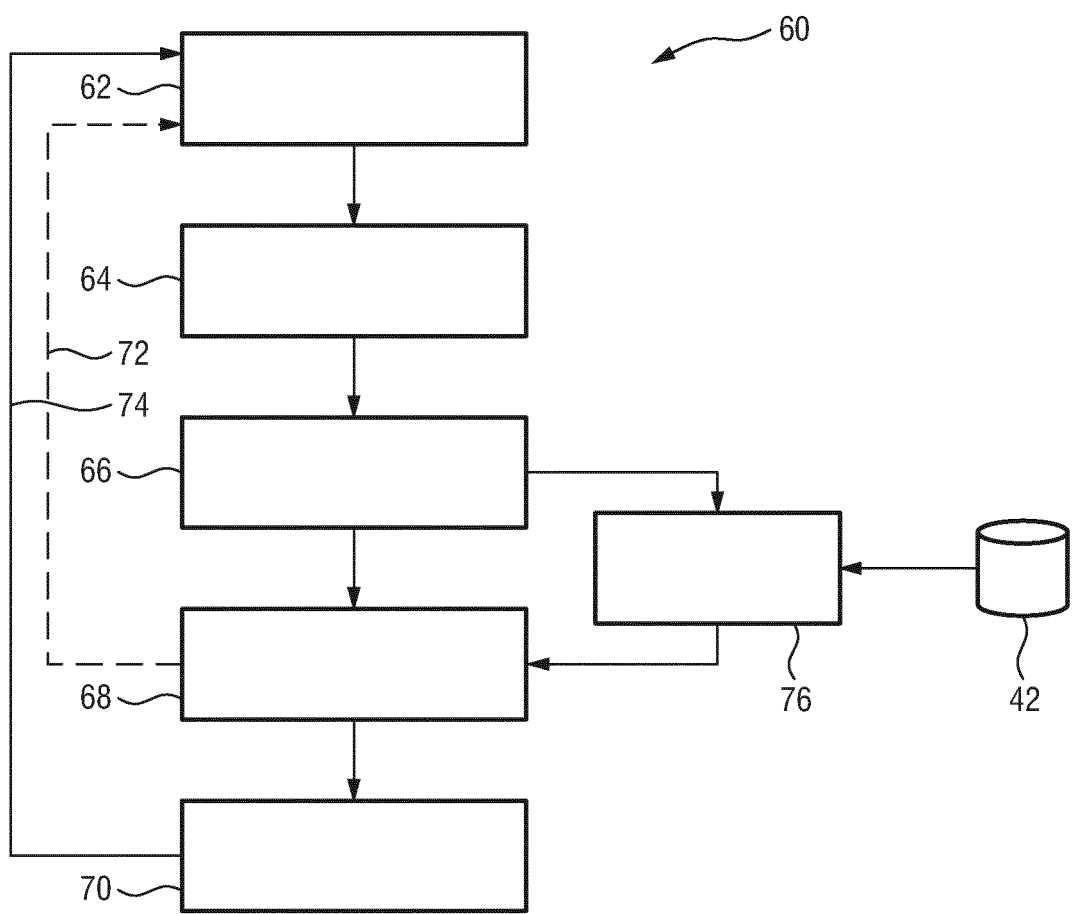
FIG. 6a shows a schematic flow diagram illustrating method steps for determining a compound image.

In FIG. 6a, a flow diagram of a method for determining the compound ultrasound image 38 from an anatomical site of the object 18 is schematically shown and generally denoted by 60. The method 60 starts with the ultrasound scan and with the receiving of the different ultrasound data sets 26, 28 at the data interface 30 as shown at step 62. The ultrasound data sets 26, 28 are segmented by the segmentation unit 32 as shown at step 64 and the reference frames 48-54 are determined as the spatial reference on the basis of the segmentation data as shown at step 66. The image generation unit 36 combines the different ultrasound data sets 26, 28 on the basis of the spatial references 48-54 and determines the compound ultrasound image 38 as shown at step 68. The compound ultrasound image 38 is provided to the display 22 in order to display the image to the user as shown at step 70.

The receiving of ultrasound data sets 26, 28 and the processing and the generation of the compound ultrasound image 38 is a continuous process and performed until the user stops the process or the system identifies that the compound ultrasound image 38 has achieved a desired level of confidence. The continuous process is indicated by the feedback loops 72, 74, wherein the loop may be performed before displaying the compound ultrasound image 38 or continuously during the displaying at step 70.

At step 76, the confidence values are determined on the basis of the spatial reference, predetermined statistical values or an ultrasound propagation model and provided to the image generation unit 36 so that the compound ultrasound image 38 can be determined on the basis of the confidence value at step 68.

Figure 6B:
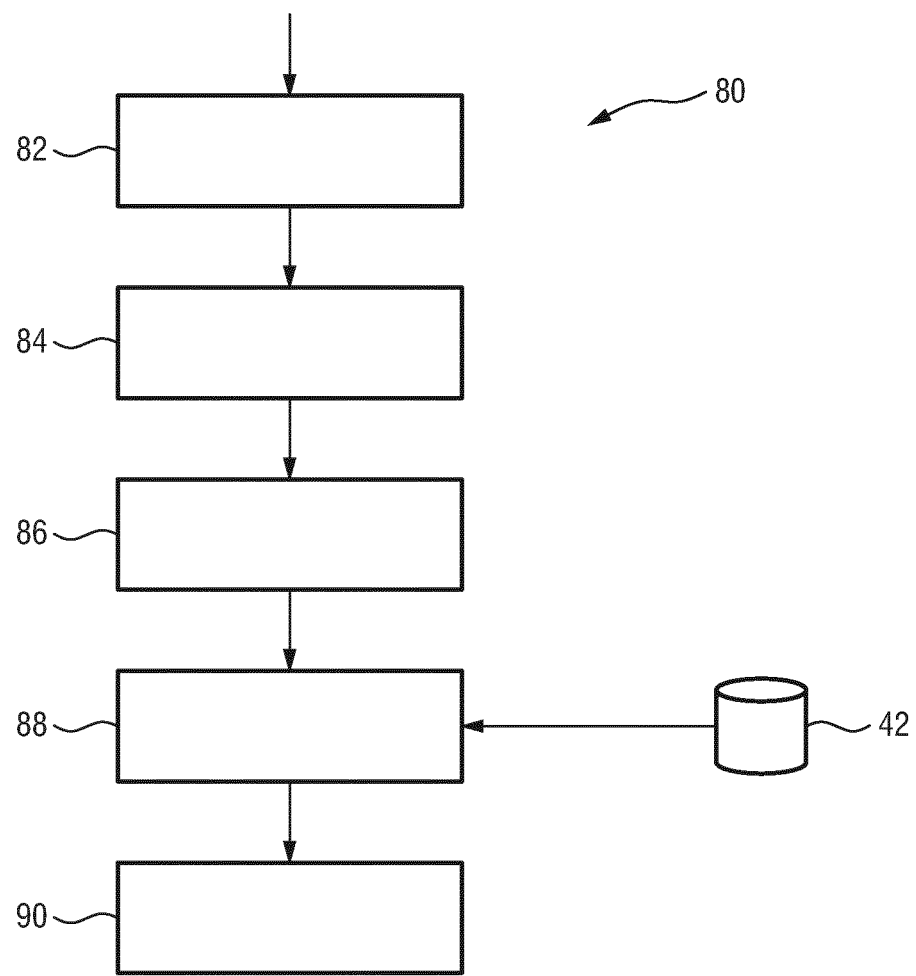
FIG. 6b shows a schematic flow diagram of a method for determining confidence values for different regions of ultrasound image data.

In FIG. 6b a method for determining the confidence values is schematically shown and generally denoted by 80. The method starts with the acquisition of an ultrasound data set in an ultrasound scan of the object 18, wherein the scan may be performed in a single viewing direction (or different viewing directions) and based on an ultrasound scan as shown at step 82. The anatomical structures of the object 18 in the ultrasound data set are segmented by the segmentation unit 32 as shown at step 84. At step 86, the reference frame 48-54 including the spatial references is determined on the basis of the segmentation data. The confidence values for different regions in the ultrasound data set are determined on the basis of the orientation of the anatomical object 18 in the field of view 16 on the basis of predefined values as a statistical map or on the basis of a propagation model received from the memory 42 or the database 42 as shown at step 88. At step 90 the ultrasound image based on the ultrasound data set and the confidence values are superposed as shown in FIG. 5a, b and provided to the display 22. The method 80 may have an additional step (not shown) similar the previous embodiment, wherein the confidence values determined in step 88 can be provided to the image generation unit 36 so that the compound ultrasound image 38 can be determined on the basis of the confidence value.

The method shown in FIG. 5b provides an alternative to indicate low confidence regions 56 in the ultrasound image data so that the reliability of the measurements can be improved with low technical effort.

The methods 60, 80 may be executed on a computer by a computer program. While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system for determining ultrasound image data from an object, comprising:
    an ultrasound probe for acquiring ultrasound data from the object, and
    an ultrasound imaging apparatus comprising:
        a data interface configured to receive ultrasound data within a field of view and resulting from an ultrasound scan of an object,
        a segmentation unit for segmenting anatomical structures of the object in the ultrasound data and arranged to provide segmentation data of the anatomical structures,
        a reference determining unit adapted to determine a spatial orientation of the anatomical object in the field of view for the ultrasound data on the basis of the segmentation data, and
        a confidence determining unit arranged to determine confidence values for different regions of the received ultrasound data on the basis of the spatial orientation of the anatomical object in the field of view and a propagation model of the ultrasound waves within said anatomical object; and
        a display for displaying the confidence values in an ultrasound image.

2. The ultrasound imaging system as claimed in claim 1, wherein the confidence values are further determined on the basis of predetermined reference values of the different regions of the object.

3. The ultrasound imaging system as claimed in claim 1, wherein one confidence value is assigned to each voxel of the ultrasound data and wherein the confidence values are stored in a confidence map.

4. The ultrasound imaging system as claimed in claim 1, wherein the ultrasound data comprise a plurality of different ultrasound data sets resulting from an ultrasound scan of an object in different viewing directions; and the ultrasound imaging apparatus further comprises an image generation unit for combining the different ultrasound data sets to a compound ultrasound image on the basis of the different spatial orientations.

5. The ultrasound imaging system as claimed in claim 4, wherein the compound image is generated on the basis of the confidence values, wherein the ultrasound data of the different regions in the different ultrasound data sets are weighted on the basis of the different confidence values to form the compound image.

6. The ultrasound imaging system as claimed in claim 5, wherein the data interface is adapted to receive the ultrasound data sets substantially simultaneously to the ultrasound scan of the object as consecutive data sets or a substantially continuous data stream, and wherein the image generation unit is adapted to generate the compound image substantially simultaneously to the received data sets.

7. A method for evaluating ultrasound image data from an anatomical site of an object, comprising the steps of:
    receiving, from a data interface operating on an ultrasound imaging apparatus coupled to an ultrasound probe, at least one ultrasound data set of the object,
    segmenting, using a segmentation unit operating on the ultrasound imaging apparatus, anatomical structures in the ultrasound data set and providing segmentation data of the anatomical structures,
    determining, using a reference determining unit operating on the ultrasound imaging apparatus, a spatial orientation of the anatomical object in the field of view for the ultrasound data set on the basis of the segmentation data, and
    determining, using a confidence determining unit operating on the ultrasound imaging apparatus, confidence values of the received ultrasound data on the basis of the spatial orientation of the anatomical object in the field of view and a propagation model of the ultrasound waves within said anatomical object.

8. The method as claimed in claim 7, further comprising:
    combining the ultrasound data sets to a compound ultrasound image on the basis of the spatial references and the confidence values, wherein the ultrasound data of the different regions in the different ultrasound data sets are weighted on the basis of the different confidence values to form the compound image.

9. The method as claimed in claim 7, wherein the object is skull of a fetus.

10. The method as claimed in claim 7, wherein the spatial orientation is determined with respect to a reference frame including a barycenter of the skull.

11. The method as claimed in claim 10, wherein the reference frame further includes eyes.

* * * * *